US009803241B2

(12) United States Patent
Sarwal et al.

(10) Patent No.: US 9,803,241 B2
(45) Date of Patent: Oct. 31, 2017

(54) METHODS AND COMPOSITIONS FOR DETERMINING A GRAFT TOLERANT PHENOTYPE IN A SUBJECT

(71) Applicant: The Board of Trustees of the Leland Stanford Junior University, Palo Alto, CA (US)

(72) Inventors: Minnie M. Sarwal, Portola Valley, CA (US); Li Li, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/270,206

(22) Filed: May 5, 2014

(65) Prior Publication Data
US 2014/0329708 A1 Nov. 6, 2014

Related U.S. Application Data

(63) Continuation of application No. 13/059,745, filed as application No. PCT/US2009/004710 on Aug. 17, 2009, now abandoned.

(60) Provisional application No. 61/089,805, filed on Aug. 18, 2008.

(51) Int. Cl.
*C12Q 1/68* (2006.01)

(52) U.S. Cl.
CPC ......... *C12Q 1/6876* (2013.01); *C12Q 1/6883* (2013.01); *C12Q 2600/118* (2013.01); *C12Q 2600/124* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,607,879 B1 | 8/2003 | Cocks et al. | |
| 7,026,121 B1 | 4/2006 | Wohlgemuth et al. | |
| 7,879,556 B2 | 2/2011 | Wohlgemuth et al. | |
| 2003/0017619 A1 | 1/2003 | Rokubo et al. | |
| 2003/0022252 A1 | 1/2003 | Thomson | |
| 2003/0104371 A1 | 6/2003 | Strom et al. | |
| 2004/0163654 A1 | 8/2004 | Williams | |
| 2005/0025769 A1 | 2/2005 | Kobayashi et al. | |
| 2006/0088836 A1 | 4/2006 | Wohlgemuth et al. | |
| 2006/0088876 A1 | 4/2006 | Bauer | |
| 2006/0246485 A1 | 11/2006 | Sarwal et al. | |
| 2006/0269949 A1 | 11/2006 | Halloran | |
| 2006/0281122 A1 | 12/2006 | Bryant et al. | |
| 2007/0031890 A1 | 2/2007 | Wohlgemuth et al. | |
| 2007/0111210 A1 | 5/2007 | Bigaud et al. | |
| 2007/0122806 A1 | 5/2007 | Strom et al. | |
| 2007/0134728 A1 | 6/2007 | Hu et al. | |
| 2007/0212701 A1 | 9/2007 | O'Toole et al. | |
| 2007/0232658 A1 | 10/2007 | Wagner et al. | |
| 2007/0264272 A1 | 11/2007 | Perreault et al. | |
| 2008/0233573 A1 | 9/2008 | Storm et al. | |
| 2008/0280282 A1 | 11/2008 | Bauer, Jr. | |
| 2009/0022730 A1 | 1/2009 | Raulf et al. | |
| 2009/0197286 A1 | 8/2009 | Karin et al. | |
| 2009/0269334 A1 | 10/2009 | Bigaud et al. | |
| 2009/0304705 A1 | 12/2009 | Grass | |
| 2010/0120629 A1 | 5/2010 | Ellis et al. | |
| 2011/0171645 A1 | 7/2011 | McManus et al. | |
| 2011/0189680 A1 | 8/2011 | Keown et al. | |
| 2011/0201519 A1 | 8/2011 | Sarwal et al. | |
| 2013/0157888 A1 | 6/2013 | Nagele | |

FOREIGN PATENT DOCUMENTS

| | | |
|---|---|---|
| EP | 1731620 A1 | 12/2006 |
| EP | 2080140 A2 | 7/2009 |
| EP | 2295966 A1 | 3/2011 |
| WO | 2004074815 A2 | 9/2004 |
| WO | 2005005601 A2 | 1/2005 |
| WO | 2005070086 A2 | 8/2005 |
| WO | 2006082390 A1 | 8/2006 |
| WO | 2007104537 A2 | 9/2007 |
| WO | 2007121922 A2 | 11/2007 |
| WO | 2008009132 A1 | 1/2008 |
| WO | 2008084331 A2 | 7/2008 |
| WO | 2009143624 A1 | 12/2009 |
| WO | 2010038974 A2 | 4/2010 |

OTHER PUBLICATIONS

Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.
"GeneChip Human Genome U133 Arrays", Affymetrix (2005).
"Affymetrix Human genome U133 Plus 2.0 Array", Gene Expression Omnibus (Nov. 2003), XP002627319, 3pgs.
Agilent-014850 whole human genome microarray 4x44K G4112F (Probe Name Version), GEO (2008), XP002594592.
Akalin et al., "Blocking Cell Microtubule Assembly Inhibits the Alloimmune Response In Vitro and Prolongs Renal Allograft Survival by Inhibition of Th1 and Sparing of Th2 Cell Function In Vivo", J Am Soc Nephrol (Jan. 1995), 5(7):1418-1425.

(Continued)

*Primary Examiner* — Nancy J Leith
(74) *Attorney, Agent, or Firm* — Kyle A. Gurley; Bret E. Field; Bozicevic, Field & Francis LLP

(57) ABSTRACT

Methods are provided for determining whether a subject has a graft tolerant phenotype. In practicing the subject methods, the expression of at least 5 genes in a sample from the subject, e.g., a blood sample, is assayed to obtain a gene expression result for the at least 5 genes. The obtained gene expression result for the at least 5 genes is then employed to determine whether the subject has a graft tolerant phenotype. Also provided are compositions, systems and kits that find use in practicing the subject methods. The methods and compositions find use in a variety of applications, including the determination of an immunosuppressive therapy regimen.

9 Claims, 6 Drawing Sheets

(56) References Cited

OTHER PUBLICATIONS

Akalin et al., "Gene expression analysis in human renal allograft biopsy samples using high-density oligoarray technology", Transplantation (Sep. 2001), 72(5):948-53.
Alarcon et al., "Time to renal disease and end-stage renal disease in Profile: a multiethnic lupus cohort", PLos Med (Oct. 2006), 3(10):e396.
Al-Lamki et al., "Expression of Tumor Necrosis Factor Receptors in Normal Kidney and Rejecting Renal Transplants", Laboratory Investigation (Nov. 2001), 81(11):1503-1515.
Braud et al., "Immunosuppresive Drug-Free Operational Immune Tolerance in Human Kidney Transplant Recipients: Part 1. Blood Gene Expression Statistical Analysis", J Cell Biochem (Apr. 2008),103(6):1681-1692.
Brouard et al., "Identification of a peripheral blood transcriptional biomarker panel associated with operational renal allograft tolerance", PNAS (Sep. 2007), 104(39):15448-15453.
Butte et al., "Protein microarrays discover angiotensinogen and PRKRIP1 as novel targets for autoantibodies in chronic renal disease", Mol Cell Proteomics (Mar. 2011), 10(3):M110.000497.
Carvalho-Gaspar et al., "Chemokine gene expression during allograft rejection: Comparison of two quantitative PCR techniques", J Immunol Methods (2005), 301(1-2):41-52.
Chan, "Integrating Transcriptomics and Proteomics", G&P magazine (2006), 6(3):20-26, printed from www.ddmag.com, 6 pages.
Chen et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.
Chen et al., "Discordant protein and mRNA expression in lung adenocarcinomas", Mol Cell Proteomics (2002), 1(4):304-13.
Cheung et al., "Natural Variation in Human Gene Expression Assessed in Lymphoblastoid Cells," Nat Genet (Mar. 2003), 33(3):422-425.
Chu et al., "Cloning of a new "finger" protein gene (ZNF173) within the class I region of the human MHC", Genomics (1995), 29(1):229-39.
Chua et al., "Applications of Microarrays to Renal Transplantation: Progress and Possibilities" Front Biosci (2003), 8:S913-23.
Communal et al., "Reciprocal modulation of mitogen-activated protein kinases and mitogen-activated protein kinase phosphatase 1 and 2 in failing human myocardium", J Card Fail (Apr. 2002), 8(2):86-92.
Cox et al., "Altered modulation of WNT-beta-catenin and PI3K/Akt pathways in IgA nephropathy", Kidney Int (Aug. 2010), 78(4):396-407.
Database Embl [Online], "Thymidine Kinase, Cytosolic (human), mRNA Sequence", (Feb. 1998), 2pages, XP002434108, Database accession No. AA778098.
Dinarello, "Anti-inflammatory Agents: Present and Future", Cell (Mar. 2010), 140(6):935-950.
Dugré et al., "Cytokine and cytotoxic molecule gene expression determined in peripheral blood mononuclear cells in the diagnosis of acute renal rejection.", Transplantation (2000), 70(7):1074-1080.
Enard et al., "Intra- and interspecific variation in primate gene expression patterns", Science (Apr. 2002), 296(5566):340-3.
Farivar et al., "The role of CC and CXC chemokines in cardiac allograft rejection in rats", Exp Mol Pathol (2005), 78(3):171-176.
Flechner et al., "Kidney transplant rejection and tissue injury by gene profiling of biopsies and peripheral blood lymphocytes", Am J Transplant (2004), 4(9):1475-89.
Fujiwaki et al., "Thymidine Kinase in Epithelial Ovarian Cancer: Relationship with the Other Pyrimidine Pathway Enzymes", Int J Cancer (2002), 99(3):328-335.
Gimino et al., "Gene Expression Profiling of Bronchoalveolar Lavage Cells in Acute Lung Rejection," Am J Respir Crit Care Med (2003), 168(10):1237-1242.
Gronowitz et al., "Serum Thymidine Kinase in Transplant Patients: Its Relation to Cytomegalovirus Activity, Renal Transplant Rejection and its Use for Monitoring of Antiviral Therapy", Ann Clin Res (1986), 18(2):71-75.
Gwinner, "Renal transplant rejection markers" World J Urol (Oct. 2007), 25(5):445-455.
Hardiman, "Microarray platforms—comparisons and contrasts", Pharmacogenomics (Jan. 2004), 5(5): 487-502.
Hauge et al., "Characterization of the FAM110 gene family", Genomics (May 2007), 90(1):14-27.
Hauser et al., "Prediction of Acute Renal Allograft Rejection by Urinary Monokine Induced by IFN-gamma (MIG)", The American Society of Nephrology (Jan. 2005), 16(6):1849-1858.
Hernandez-Fuentes; et al., "Immunologic monitoring", Immunol Rev (2003), 196:247-264.
Hidalgo et al., "The Transcriptome of Human Cytotoxic T Cells: Measuring the Burden of CTL-Associated Transcripts in Human Kidney Transplants", American Journal of Transplantation (Mar. 2008), 8(3):637-646.
Hillier et al., "Generation and annotation of the DNA sequences of human chromosomes 2 and 4", Nature (2005), 434(7034):724-731.
Horwitz et al., "Detection of Cardiac Allograft Rejection and Response to Immunosuppressive Therapy with Peripheral Blood Gene Expression," Circulation (2004), 110(25):3815-3821.
Ismail, "Important fluorinated drugs in experimental and clinical use", J Fluori Chem (Dec. 2002), 118(1):27-33.
Jevnikar et al., "Late Kidney Allograft Loss: What We Know About It, and What We Can Do About It", Clin J Am Soc Nephrol (2008), 3(Suppl2):S56-S67.
Joosten et al., "Chronic Renal Allograft Rejection: Pathophysiologic Considerations", Kidney Int (2005), 68(1):1-13.
Kalil et al., "Meta-analysis: the efficacy of strategies to prevent organ disease by cytomegalovirus in solid organ transplant recipients", Ann Intern Med (Dec. 2005), 143(12):870-880.
Kaposztas et al., "Impact of rituximab therapy for treatment of acute humoral rejection", Clin Transplant (Jan.-Feb. 2009), 23(1):63-73.
Lang et al., "DUSP meet immunology: dual specificity MAPK phosphatases in control of the inflammatory response", J Immunol (Dec. 2006), 177(11):7497-504.
Lee et al., "Expression profiling of murine double-negative regularoty T cells suggest mechanisms for prolonged cardiac allograft survival", J. Immunol. (2005), 174(8):4535-4544.
Li et al., "A Peripheral Blood Diagnostic Test for Acute Rejection in Renal Transplantation", Am J Transplant (Oct. 2012), 12(10):2710-2718.
Li et al., "Identifying compartment-specific non-HLA targets after renal transplantation by integrating transcriptome and "antibodyome" measures", PNAS (2009), 106(11):4148-4153.
Li et al., "Interference of globin genes with biomarker discovery for allograft rejection in peripheral blood samples", Physiol Genomics (Jan. 2008), 32(2):190-197.
Ling et al., "Integrative urinary peptidomics in renal transplantation identifies biomarkers for acute rejection", J Am Soc Nephrol (Apr. 2010), 21(4):646-653.
Mansfield et al., "Arraying the Orchestration of Allograft Pathology", Am J Transplant (2004), 4(6):853-62.
Marsden, "Predicting Outcomes after Renal Transplantation—New Tools and Old Tools," N Eng J Med (2003), 349(2):182-184.
Martinez-Llordella et al., "Using transcriptional profiling to develop a diagnostic test of operational tolerance in liver transplant recipients", J Clin Invest (Aug. 2008), 118(8):2845-2857.
Matsuki et al., "Novel regulation of MHC class II function in B cells", EMBO J (Jan. 2007), 26(3):846-854.
McMorrow et al., "New intra-renal graft genes associated with tolerance or rejection", Kidney Int (2002), 61(1 Suppl): S85-S93.
Medbury et al., "The Cytokine and Histological Response in Islet Xenograft Rejection is Dependent Upon Species Combination," Transplantation (1997), 64(9):1307-1314.
Mengel et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.

(56) References Cited

OTHER PUBLICATIONS

Metz et al., "Application of proteomics in the discovery of candidate protein biomarkers in a diabetes autoantibody standardization program sample subset", J Proteome Res (Feb. 2008), 7(2):698-707.
Midha et al., "Chemokine Expression in Nerve Allografts," Neurosurgery (2004), 54(6):1472-1479.
Morgun et al., "Molecular Profiling Improves Diagnoses of Rejected and Infection in Transplanted Organs", Circulation Research (Jun. 2006), 98(12):e74-83.
Nesslinger et al., "A viral vaccine encoding prostate-specific antigen induces antigen spreading to a common set of self-proteins in prostate cancer patients", Clinical Cancer Research (Aug. 2010), 16(15):4046-4056.
O'Riordan et al., "Bioinformatic Analysis of the Urine Proteome of Acute Allograft Rejection," J Am Soc Nephrol (2004), 15(12):3240-3248.
Roedder et al., "The pits and pearls in translating operational tolerance biomarkers into clinical practice", Curr Opin Organ Transplant (Dec. 2012), 17(6):655-662.
Rotondi et al., "High pretransplant serum levels of CXCL9 are associated with increased risk of acute rejection and graft failure in kidney graft recipients", Transpl Int (May 2010), 23(5):465-475.
Saint-Mezard et al., "Analysis of independent microarray datasets of renal biopsies identifies a robust transcript signature of acute allograft rejection", Transplant Int (Mar. 2009), 22(3):293-302.
Sarwal et al., "Integrative Genomics to Identify Non-HLA Allogenic Kidney-Specific Targets after Kidney Transplantation", Transplantation (2008), 86(2S):13, Oral Abstracts, downloaded Apr. 6, 2010.
Sarwal et al., "Molecular Heterogeneity in Acute Renal Allograft Rejection Identified by DNA Microarray Profiling," N Eng J Med (2003), 349(2):125-138.
Sato et al., "Aberrant CD3- and CD28-mediated signaling events in cord blood T Cells are associated with dysfunctional regulation of Fas ligand-mediated cytotoxicity", J Immunol (Apr. 1999), 162(8):4464-4471.
Scherer et al., "Early Prognosis of the Development of Renal Chronic Allograft Rejection by Gene Expression Profiling of Human Protocol Biopsies", Transplantation (2003), 75(8):1323-30.
Serody et al., "T-lymphocyte production of macrophage inflammatory protein-1alpha is critical to the recruitment of CD8(+) T cells to the liver, lung, and spleen during graft-versus-host disease", Blood (2000), 96(9):2973-2980.
Shi et al., "[Clinical significance of RANTES and MIP-1 alpha in acute rejection episode in kidney transplantation]", Zhongguo Yi Xue Ke Xue Yuan Xue Bao (2004), 26(1):70-72,abstract.
Sigdel et al., "Shotgun proteomics identifies proteins specific for acute renal transplant rejection", Proteomics Clin Appl (Jan. 2010), 4(1):32-47.
Sigdel et al., "Profiling of autoantibodies in IgA nephropathy, an integrative antibiomics approach", Clin J Am Soc Nephrol (Dec. 2011), 6(12):2775-2784.
Simon et al., "Serial Peripheral Blood Perforin and Granzyme B Gene Expression Measurements for Prediction of Acute Rejection in Kidney Graft Recipients," Am J Transplant (2003), 3(9):1121-1127.
Teramoto et al., "DNA Synthesis in Hepatocytes During Liver Allograft Rejection in Rats", Transplantation (1990), 50(2):199-201.
Thomson et al., "Monitoring the Patient Off Immunosuppression. Conceptual framework for a proposed tolerance assay study in liver transplant recipients" Transplantation (2001), 72(8 Suppl):S13-S22.
Voshol et al., "Evaluation of biomarker discovery approaches to detect protein biomarkers of acute renal allograft rejection", J Proteome Res (Jul.-Aug. 2005), 4(4):1192-1199.
Wakui et al., "Genes Highly Expressed in the Early Phase of Murine Graft-Versus-Host Reaction," Biochem Biophys Res Commun (2001), 282(1):200-206.
Whitfield et al., "Systemic and Cell Type-Specific Gene Expression Patterns in Scleroderma Skin," PNAS (2003), 100(21):12319-12324.
Wu, "Analysing Gene Expression Data From DNA Microarrays to Identify Candidate Genes," J Pathol (2001), 195(1):53-65.
Zhang et al., "Microarray Analysis of Gene Expression in Peripheral Blood Mononuclear Cells Derived From Long-Surviving Renal Recipients", Transplant Proc (2002), 34(5):1757-1759.
"GeneChip 3' IVT Plus Reagent Kit", Affymetrix (2013), User Manual, 45 pgs.
Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.
Kazutoshi Takahashi et al: "Induction of Pluripotent Stem Cells from Adult Human Fibroblasts by Defined Factors", Cell, Cell Press, US, vol. 131, No. 5, Nov. 30, 2007 (Nov. 30, 2007), pp. 861-872, ISSN: 0092-8674, DOI: 10.1016/J.CELL.2007.11.019.
Ishoku, "VI. cDNA microarray analysis" Journal of the Japan Society for Transplantation, (transplantation), (2004), 39, [2], p. 138-144.
Anglicheau et al. "Noninvasive Prediction of Organ Graft Rejection and Outcome Using Gene Expression Patterns" Transplantation, vol. 86, No. 2, Jul. 27, 2008, pp. 192-199.
Åsberg et al. "Bilateral Pharmacokinetic Interaction Between Cyclosporine A and Atorvastatin in Renal Transplant Recipients", American Journal of Transplantation 2001, vol. 1, pp. 382-386.
Schade et al. "Dasatinib, a small-molecule protein tyrosine kinase inhibitor, inhibits T-cell activation and proliferation", Blood, vol. 111, No. 3, Feb. 1, 2008, pp. 1366-1377.
Patil et al. "Bronchoalveolar Lavage Cell Gene Expression in Acute Lung Rejection: Development of a Diagnostic Classifier", Transplantation, Jan. 27, 2008, vol. 85, No. 2, pp. 224-231.

METHODS AND COMPOSITIONS FOR DETERMINING A GRAFT TOLERANT PHENOTYPE IN A SUBJECT

GOVERNMENT RIGHTS

This invention was made with Government support under contract AI061739 awarded by the National Institutes of Health. The Government has certain rights in the invention.

BACKGROUND OF THE INVENTION

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host.

A variety of immunosuppressive agents have been employed in transplantation procedures, including azathioprine, methotrexate, cyclophosphamide, FK-506, rapamycin and corticosteroids. Agents finding increased use in immunosuppressive therapy due to their preferential effect on T-cell mediated reactions are the cyclosporins.

Following transplantation, administration of the immunosuppressive agent must be continued indefinitely since the benefits of immunosuppressive therapy are reversible and graft rejection may occur once administration of the immunosuppressive agent is discontinued. While use of immunosuppressive agents, such as Cyclosporin A, has been reported to prolong the survival of allogeneic transplants involving skin, heart, kidney, pancreas, bone marrow, small intestine and lung, use of such agents is not without undesirable side effects. Examples of undesirable side effects include increased risk of development of neoplastic disease conditions, e.g., skin cancer, lymphoma, etc.

While most recipients who discontinue their immunosuppressive treatment following a graft go on to suffer rejection, not all subjects suffer graft rejection. In a few cases, individuals tolerate their graft without immunosuppression, suggesting that immune non-responsiveness can be achieved in clinical practice. The mechanisms of this process are not well understood, but may involve a combination of clonal deletion, clonal anergy and the generation of active regulatory T cells.

Because of the undesirable sides effects and risks of long term immunosuppressive therapy, it would be desirable to be able identify those individuals who are tolerant to their graft, i.e., graft tolerant, so that immunosuppression could be reduced or even discontinued in those individuals. Of particular interest would be the development of a way to identify graft tolerant individuals without first discontinuing immunosuppressive therapy, thereby avoiding the risk of graft rejection and damage to the graft associated therewith. The present invention meets this need.

RELEVANT LITERATURE

Publications of interest include: United States Patent Publication No. 2003/0104371; published PCT application No. WO 2005/070086; Brouard et al., PNAS 2007, vol. 104, pp. 15448-15453.

SUMMARY OF THE INVENTION

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The subject methods and compositions find use in a variety of applications, including the determination of an immunosuppressive therapy regimen.

Aspects of the present invention include methods of determining whether a subject who has received an allograft has a graft tolerant phenotype, the method including: (a) evaluating the level of expression of at least 5 genes in a sample from the subject to obtain a gene expression result, wherein the at least 5 genes are selected from either Table 2 or Table 4; and (b) determining whether the subject has a graft tolerant phenotype based on the gene expression result. In certain embodiments, the allograft is a renal allograft. In certain embodiments, the sample is a blood sample, e.g., a peripheral blood sample. In certain embodiments, the evaluating step comprises assaying the sample for an expression product of the at least 5 genes. In certain embodiments, the expression product is selected from one both of: a nucleic acid transcript and a protein. In certain embodiments, the expression product is a nucleic acid transcript and the evaluating step comprises performing one or more of the following: a RT-PCR assay, a microarray assay, and a Northern blot. In certain of these embodiments, the microarray is a genomic array. In certain embodiments, the expression product is a protein and the evaluating step comprises employing a proteomic array. In certain embodiments, and the expression level of at least 10 genes from either Table 2 or Table 4 is evaluated. In certain embodiments, the expression level of all of the genes from either Table 2 or Table 4 is evaluated. In certain embodiments, the determining step comprises comparing the gene expression result to a reference gene expression profile. In certain embodiments, the reference gene expression profile is selected from: a graft tolerant phenotype gene expression profile and a graft intolerant phenotype gene expression profile.

Aspects of the present invention include methods of managing immunosuppressive therapy treatment in a subject having an allograft, the method comprising: (a) determining whether the subject has a graft tolerant phenotype as described above; and (b) managing future immunosuppressive therapy treatment in the subject based on the determining step (a). In certain embodiments, the method comprises at least reducing immunosuppression in the subject if said subject is found to have a graft tolerant phenotype. In certain embodiments, the method comprises discontinuing immunosuppression in the subject if the subject is found to have a graft tolerant phenotype.

Aspects of the present invention include systems for determining whether a subject who has received an allograft has a graft tolerant phenotype, the system comprising: (a) a gene expression evaluation element for evaluating the level of expression of at least 5 genes in a sample from the subject to obtain a gene expression result, wherein the at least 5 genes are selected from either Table 2 or Table 4; and (b) a graft tolerance determination element for employing the gene expression result to determining whether the subject has a graft tolerant phenotype. The output of the subject systems is in a user-readable format. Such formats include, but are not limited to: a file stored in a memory that is accessible to a user, displayed to a user on graphical user interface (GUI), sent to a user via the internet, e.g., on a web page or as an email, etc. As such, in certain embodiments, systems of the invention include a communications module having input and output managers that regulate communication between the system and a user. In certain embodiments, the gene expression evaluation element comprises at least one reagent for assaying a sample for an expression product of the at least 5 genes. In certain embodiments, the expression product of the at least one gene is selected from: a nucleic acid transcript and a protein. In certain embodiments, the expression level all of the genes in either Table 2 or Table 4 is assessed.

Aspects of the present invention include kits for determining whether a subject who has received an allograft has a graft tolerant phenotype, the kit comprising: (a) a gene expression evaluation element for evaluating the level of expression of at least 5 genes in a sample from the subject to obtain a gene expression result, wherein the at least 5 genes are selected from either Table 2 or Table 4; and (b) a phenotype determination element for employing the gene expression result to determine whether the subject has a graft tolerant phenotype. In certain embodiments, the kite further includes instructions for using the gene expression evaluation and phenotype determination elements to determine whether a subject has a graft tolerant phenotype. In certain embodiments, the gene expression evaluation element comprises at least one reagent for evaluating a sample for an expression product of the gene. In certain embodiments, the expression product of the at least one gene is selected from: a nucleic acid transcript and a protein. In certain embodiments the gene expression evaluation element is selected form: a microarray and a collection of gene specific primers, where in certain embodiments the kits include both of these components. In certain embodiments, the expression level all of the genes in one or both of Table 2 or Table 4 is assessed. In certain embodiments, the phenotype determination element comprises a reference expression value for the at least one gene. In certain embodiments, the phenotype determination element comprises a reference expression profile that includes a reference expression value for at least one additional gene. In certain embodiments, the reference expression profile is a graft tolerant phenotype expression profile. In certain embodiments, the reference expression profile is a graft intolerant phenotype expression profile.

Aspects of the present invention include computer program products for determining whether a subject who has undergone a renal allograft has a graft tolerant phenotype, wherein the computer program product, when loaded onto a computer, is configured to employ a gene expression result from a sample derived from the subject to determining whether a subject who has undergone a renal allograft has a graft tolerant phenotype, wherein the gene expression result comprises expression data for at least one gene from Table 2 or Table 4.

Also provided are reference expression profiles for a phenotype that is one of: (a) graft tolerant; or (b) graft intolerant; wherein the expression profile is recorded on a computer readable medium that is accessible by a user, e.g., in a user readable format. In certain embodiments, the expression profile includes at least 5 genes from either one or both of Tables 2 or 4. In certain embodiments, the expression profile is a profile for a phenotype that is allograft tolerant. In certain embodiments, the expression profile is a profile for a phenotype that is graft intolerant.

Also provided by the invention is a collection of reagents for evaluating gene expression, where the collection includes: reagents specific for at least 5 of the genes in either one or both of Tables 2 or 4. In certain embodiments, the reagents are gene specific primers. In certain embodiments, the collection comprises at least 10 gene specific primers. Also provided are arrays of probe nucleic acids immobilized on a solid support, where the arrays include: a plurality of probe nucleic acid compositions, wherein each probe nucleic acid composition is specific for a gene whose expression profile is indicative of a graft tolerance, e.g., allograft tolerance, wherein at least two of the probe nucleic acid compositions correspond to genes listed in one or both of Tables 2 and 4.

BRIEF DESCRIPTION OF THE FIGURES

In FIG. 2, the left panel shows the training set and the right panel shows the test set. All spontaneous samples are 100% predicted correctly using this 24 gene set. The LK2 induced patient (TOL_LK2) was predicted as SP TOL, which has been confirmed by clinical observation. The patient has been off drug for 2 years.

DESCRIPTION OF THE SPECIFIC EMBODIMENTS

Figure 1A:
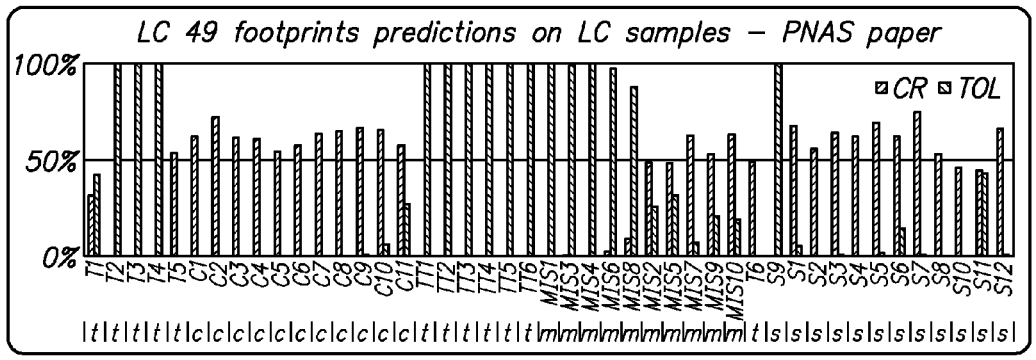
FIG. 1A shows LC 49 gene foot prints prediction on a set of LC samples (see Brouard et al., PNAS 2007, vol. 104, pp. 15448-15453).

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The methods and compositions find use in a variety of applications, including the determination of an immunosuppressive therapy regimen.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention is directed to methods of determining whether a subject has a graft tolerant phenotype, as well as reagents and kits for use in practicing the subject methods. In further describing the invention, the subject methods are described first, followed by a review of the reagents and kits for use in practicing the subject methods.

Methods of Determining Whether a Subject has a Graft Tolerant Phenotype

The subject invention provides methods of determining whether a patient or subject has a graft tolerant phenotype. By graft tolerant phenotype is meant that the subject does not reject a graft organ, tissue or cell(s) that has been introduced into/onto the subject. In other words, the subject tolerates or maintains the organ, tissue or cell(s) that has been transplanted to it. As in known in the transplantation field, the graft organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host.

In practicing the subject methods, a subject or patient sample, e.g., cells or collections thereof, e.g., tissues, is assayed to determine whether the host from which the assayed sample was obtained is graft tolerant, i.e., has a graft tolerant phenotype. Accordingly, the first step of the subject methods is to obtain a suitable sample from the subject or patient of interest, i.e., a patient on immunosuppressive therapy and having at least one graft, e.g., allograft. The sample is derived from any initial suitable source, where sample sources of interest include, but are not limited to, many different physiological sources, e.g., CSF, urine, saliva, tears, tissue derived samples, e.g., homogenates, and blood or derivatives thereof.

In certain embodiments, a suitable initial source for the patient sample is blood. As such, the sample employed in the subject assays of these embodiments is generally a blood-derived sample. The blood derived sample may be derived from whole blood or a fraction thereof, e.g., serum, plasma, etc., where in many embodiments the sample is derived from blood cells harvested from whole blood. Of particular interest as a sample source are peripheral blood lymphocytes (PBL). Any convenient protocol for obtaining such samples may be employed, where suitable protocols are well known in the art.

In practicing the subject methods, the sample is assayed to obtain an expression evaluation, e.g., expression profile, for one or more genes, where the term expression profile is used broadly to include a genomic expression profile, e.g., an expression profile of nucleic acid transcripts, e.g., mRNAs, of the one or more genes of interest, or a proteomic expression profile, e.g., an expression profile of one or more different proteins, where the proteins/polypeptides are expression products of the one or more genes of interest. As such, in certain embodiments the expression of only one gene is evaluated. In yet other embodiments, the expression of two or more, e.g., about 5 or more, about 10 or more, about 15 or more, about 25 or more, about 50 or more, about 100 or more, about 200 or more, etc., genes is evaluated. Accordingly, in the subject methods, the expression of at least one gene in a sample is evaluated. In certain embodiments, the evaluation that is made may be viewed as an evaluation of the transcriptosome, as that term is employed in the art. See e.g., Gomes et al., Blood (2001 Jul. 1) 98(1):93-9.

In generating the expression profile, in many embodiments a sample is assayed to generate an expression profile that includes expression data for at least one gene/protein, usually a plurality of genes/proteins, where by plurality is meant at least two different genes/proteins, and often at least about 5, typically at least about 10 and more usually at least about 20 different genes/proteins or more, such as 50 or more, 100 or more, etc.

In the broadest sense, the expression evaluation may be qualitative or quantitative. As such, where detection is qualitative, the methods provide a reading or evaluation, e.g., assessment, of whether or not the target analyte, e.g., nucleic acid or expression product, is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid in the sample being assayed. In such embodiments, the quantitative detection may be absolute or, if the method is a method of detecting two or more different analytes, e.g., target nucleic acids, in a sample, relative. As such, the term "quantifying" when used in the context of quantifying a target analyte, e.g., nucleic acid(s), in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

Genes/proteins of interest are genes/proteins that are differentially expressed or present at different levels in graft tolerant versus graft intolerant individuals. Representative genes/proteins of interest in certain embodiments include, but are not limited to, the genes/proteins provided in Tables 1, 2, 3 and 4. Note that for all of the gene tables shown herein, detailed information for each specific gene, including nucleotide sequence information, can be retrieved through the NCBI Entrez nucleotide database at located at the website: http(colon)//www(dot)ncbi.nlm.nih(dot)gov/ by selecting "Gene" as the database and entering the Entrez Gene ID number listed into the search window.

In certain embodiments, at least one of the genes/proteins in the prepared expression profile is from Tables 1, 2, 3 and/or 4, where the expression profile may include expression data for 5, 10, 20, 50, 75 or more of, including all of, the genes/proteins listed in Tables 1, 2, 3 and/or 4. In certain embodiments, at least 5 genes in Table 2 and/or Table 4 are evaluated, including 10 or more, 20 or more or all of the genes in Table 2 and/or Table 4. The number of different genes/proteins whose expression and/or quantity data, i.e., presence or absence of expression, as well as expression/quantity level, that are included in the expression profile that is generated may vary, but may be at least 2, and in many embodiments ranges from 2 to about 100 or more, sometimes from 3 to about 75 or more, including from about 4 to about 70 or more.

In certain embodiments, the expression profile obtained is a genomic or nucleic acid expression profile, where the amount or level of one or more nucleic acids in the sample is determined, e.g., the nucleic acid transcript of the gene of interest. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via biopsy of tissue, using standard protocols, where cell types or tissues from which such nucleic acids may be generated include any tissue in which the expression pattern of the to be determined phenotype exists, including, but not limited to, peripheral blood lymphocyte cells, etc., as reviewed above.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the levels of one or more nucleic acids in a sample may be employed, including those based on amplification protocols, e.g., Polymerase Chain Reaction (PCR)-based assays, including quantitative PCR, reverse-transcription PCR (RT-PCR), real-time PCR, and the like.

Where the expression profile is a protein expression profile, any convenient protein quantitation protocol may be employed, where the levels of one or more proteins in the assayed sample are determined. Representative methods include, but are not limited to: proteomic arrays, flow cytometry, standard immunoassays (e.g., western blot, ELISA assays), etc.

Following obtainment of the expression profile from the sample being assayed, the expression profile is compared with a reference or control profile to determine the particular graft tolerant/intolerant phenotype of the cell or tissue, and therefore host, from which the sample was obtained/derived. The terms "reference" and "control" as used herein mean a standardized pattern of gene expression or levels of expression of certain genes to be used to interpret the expression signature of a given patient and assign a graft tolerant/intolerant phenotype thereto. The reference or control profile may be a profile that is obtained from a cell/tissue known to have the desired phenotype, e.g., tolerant phenotype, and therefore may be a positive reference or control profile. In addition, the reference/control profile may be from a cell/tissue known to not have the desired phenotype, e.g., an intolerant phenotype, and therefore be a negative reference/control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The comparison of the obtained expression profile and the one or more reference/control profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the control/reference profile(s), which similarity/dissimilarity information is employed to determine the phenotype of the cell/tissue being assayed. For example, similarity with a positive control indicates that the assayed cell/tissue has a tolerant phenotype. Likewise, similarity with a negative control indicates that the assayed cell/tissue has an intolerant phenotype.

Depending on the type and nature of the reference/control profile(s) to which the obtained expression profile is compared, the above comparison step yields a variety of different types of information regarding the cell/tissue that is assayed. As such, the above comparison step can yield a positive/negative determination of a tolerant phenotype of an assayed cell/tissue. In many embodiments, the above-obtained information about the cell/tissue being assayed is employed to diagnose a host, subject or patient with respect to that host's graft tolerance, as described above.

The subject methods further find use in pharmacogenomic applications. In these applications, a subject/host/patient is first diagnosed for the presence or absence of the graft tolerant phenotype using a protocol such as the diagnostic protocol described in the preceding section. The subject is then treated using a protocol whose suitability is determined using the results of the diagnosis step. More specifically, where the identified phenotype is tolerant, a protocol that may include a reduced level of immunosuppression (i.e., immunosuppression at a level less than that which is indicated for patients not known to be graft tolerant), or no immunosuppression, may be employed to manage/treat the subject. Alternatively, where a patient is identified as having an intolerant phenotype, full immunosuppressive protocols may be employed/continued.

In many embodiments, a host is screened for the presence of a graft tolerant phenotype following receipt of a graft or transplant. The host may be screened once or serially following transplant receipt, e.g., weekly, monthly, bimonthly, half-yearly, yearly, etc., as long as the host is on immunosuppressive therapy. In certain embodiments, monitoring of the host expression profile even after immunosuppressive therapy has been reduced or discontinued is conducted to determine whether the host has maintained the tolerogenic expression profile and may continue for the lifetime of the host.

Databases of Expression Profiles of Phenotype Determinative Genes

Also provided are databases of expression profiles of graft tolerant phenotype determinative genes. Such databases will typically comprise expression profiles of various cells/tissues having graft tolerant phenotypes, negative expression profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above-described expression profiles of phenotype determinative genes, i.e., a gene expression evaluation element made up of one or more reagents.

One type of such reagent is an array of probe nucleic acids in which the phenotype determinative genes of interest are represented. A variety of different array formats are known in the art, with a wide variety of different probe structures, substrate compositions and attachment technologies (e.g., dot blot arrays, microarrays, etc.). Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Tables 1, 2, 3 and/or 4. In certain embodiments, the number of genes that are from Tables 1, 2, 3 and/or 4 that is represented on the array is at least 5, at least 10, at least 25, at least 50, at least 75 or more, including all of the genes listed in Tables 1, 2, 3 and/or 4. In certain embodiments, the arrays include at least 5 genes listed in Table 2 and/or Table 4, including 10 or more, 20 or more or all of the genes in Table 2 and/or Table 4. The subject arrays may include only those genes that are listed in Tables 1, 2, 3 and/or 4, or they may include additional genes that are not listed in Tables 1, 2, 3 and/or 4. Where the subject arrays include probes for such additional genes, in certain embodiments the number % of additional genes that are represented does not exceed about 50%, usually does not exceed about 25%. In many embodiments where additional "non-Table 1" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in one Tables 1, 2, 3 and/or 4, often a plurality of these genes, e.g., at least 2, 5, 10, 15 or more. In certain embodiments, the number of genes that are from Tables 1, 2, 3 and/or 4 that have primers in the collection is at least 5, at least 10, at least 25, at least 50, at least 75 or more, including all of the genes listed in Tables 1, 2, 3 and/or 4. In certain embodiments, the subject gene specific primers collections include at least 5 genes listed in Table 2 and/or Table 4, including 10 or more, 20 or more or all of the genes in Table 2 and/or Table 4. The subject gene specific primer collections may include only those genes that are listed in Tables 1, 2, 3 and/or 4, or they may include primers for additional genes that are not listed in Tables 1, 2, 3 and/or 4. Where the subject gene specific primer collections include primers for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

The kits of the subject invention may include the above-described arrays and/or gene specific primer collections. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The subject kits may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for practicing one or more of the above-described methods. The subject systems may vary greatly, but typically include at least a gene expression evaluation element, e.g., one or more reagents, and a phenotype determination element.

Reagents of interest include reagents specifically designed for use in production of the above-described expression profiles of phenotype determinative genes, i.e., a gene expression evaluation element made up of one or more reagents. One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Tables 1, 2, 3 and/or 4. In certain embodiments, the number of genes that are from Tables 1, 2, 3 and/or 4 that is represented on the array is at least 5, at least 10, at least 25, at least 50, at least 75 or more, including all of the genes listed in Tables 1, 2, 3 and/or 4. In certain embodiments, the arrays include at least 5 genes listed in Table 2 and/or Table 4, including 10 or more, 20 or more or all of the genes in Table 2 and/or Table 4. The subject arrays may include only those genes that are listed in Tables 1, 2, 3 and/or 4, or they may include additional genes that are not listed in Tables 1, 2, 3 and/or 4. Where the subject arrays include probes for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in one Tables 1, 2, 3 and/or 4, often a plurality of these genes, e.g., at least 2, 5, 10, 15 or more. In certain embodiments, the number of genes that are from Tables 1, 2, 3 and/or 4 that have primers in the collection is at least 5, at least 10, at least 25, at least 50, at least 75 or more, including all of the genes listed in Tables 1, 2, 3 and/or 4. In certain embodiments, the subject gene specific primers collections include at least 5 genes listed in Table 2 and/or Table 4, including 10 or more, 20 or more or all of the genes in Table 2 and/or Table 4. The subject gene specific primer collections may include only those genes that are listed in Tables 1, 2, 3 and/or 4, or they may include primers for additional genes that are not listed in Tables 1, 2, 3 and/or 4. Where the subject gene specific primer collections include primers for such additional genes, in certain embodiments the number % of additional genes that are represented does not exceed about 50%, usually does not exceed about 25%. In many embodiments where additional "non-Table 1", "non-Table 2", "non-Table 3" or "non-Table 4" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are phenotype determinative genes.

The systems of the subject invention may include the above-described arrays and/or gene specific primer collections. The systems may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The systems may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

The following examples are offered by way of illustration and not by way of limitation.

Experimental

I. Methods and Materials

We performed 80 Agilent whole human genome arrays, which include approximately 43,000 probes, on samples from the following subjects: 15 Stanford spontaneous tolerances (SP-TOL or SP), 20 Immune Tolerance Network (ITN) spontaneous tolerances, 16 induced tolerances (IN-TOL or IN), 9 chronic (CAN), 8 healthy donor (HD), and 12 stable patients. We used 5 Stanford spontaneous tolerance samples and 5 chronic samples as our training set for 2-class (TOL vs. CAN) biomarker discovery, all others are as our test set. We used 14 Stanford spontaneous tolerance samples, 8 healthy donor samples, and 9 chronic samples as our training set for 3-class (HD vs. TOL vs. CAN) biomarker discovery, all others are as our test set for the prediction.

Patient and Materials

Peripheral whole blood samples were collected from 72 renal transplant patients (tolerant, stable) and 8 normal controls enrolled in this study. The protocol was approved by IRB and required written informed consent. To generate informative biomarkers by microarray for spontaneous tolerance, samples were chosen from 4 clinical phenotypes: 1) Immunosuppressive drug-free, spontaneous tolerant (SP-TOL): patients with long-term stable graft function, without immunosuppression for at least 2 years. Stable graft function was defined as stable Schwardz calculated creatinine clearance >60 mls/min/1.73 m2 with absent or low grade proteinuria (<1.5 g/day). 2) Induced tolerant (IN-TOL): patients with stable graft function were induced to accept transplanted organ through a processing of control weaning immunosuppressive drug after transplantation. 3) Chronic rejection (CAN): This group was defined according to clinical and histological criteria. All CAN patients had a progressive degradation of their renal function (creatinine clearance <60 mls/min/1.73 $m^2$ and/or proteinuria >1.5 g/day) and histological signs of vascular chronic rejection defined as endarteritis and allograft glomerulopathy with basement membrane duplication. 4) Healthy donors (HD) were included as controls. They all had a normal blood formula and no infectious or other concomitant pathology for at least 6 months prior to the study.

RNA Extraction

Whole blood was collected in PAXgene Blood RNA Tubes (PreAnalytiX, Qiagen), and total RNA was extracted using the PAXgene Blood RNA Kit (PreAnalytiX, Qiagen). PBMCs were purified using standard Ficoll-Paque gradient centrifugation according to the instructions of the manufacturer (GE Healthcare, Sweden). Total RNA was extracted using RNeasy Plus Mini Kit (Qiagen.) Total RNA concentration was measured by NanoDrop ND-1000 (NanoDrop Technologies, Wilmington, Del.), and the integrity of the extracted total RNA was assessed with the Agilent 2100 Bioanalyzer using RNA Nano Chips (Agilent Technologies, Santa Clara, Calif.). Total RNA was stored at −80° C. until sample preparation for the microarray experiments.

Microarray Hybridization and Data Analysis.

RNA samples (test and reference) were labeled using the Agilent low RNA input fluorescent linear amplification Kit (p/n 5188-5340) according to the manufacturer's instructions. To avoid confounding by extraneous factors, all the experiments were performed with a single batch and processed by one technician on the same day for each step. Briefly, 100 ng of total RNA was reverse transcribed. Amplification and labeling were performed by T7-polymerase in vitro transcription, to give fluorescent-labeled cRNA. Test and reference cRNAs were labeled with Cyanine-5 and Cyanine-3 CTP dyes. The dye incorporation rate was assessed with a NanoDrop ND-1000 spectrophotometer. Hybridization was carried out using the Agilent oligonucleotide microarray hybridization kit (p/n 5188-5242), following the manufacturer's instructions. Briefly, 825 ng of test sample cRNA was mixed with 825 ng of reference sample cRNA in the presence of target controls. This solution was subjected to fragmentation (30 min at 60° C.) and then hybridization on 44K Human Whole-Genome 60-mer oligo-chips (G4112F, Agilent Technologies) in Agilent hybridization. Slides were disassembled and washed according to the manufacturer's instructions. Microarrays were scanned with an Agilent microarray scanner (Agilent dual laser DNA microarray scanner G2565BA, Agilent technologies, Palo Alto, Calif. USA).

GeneSpring (Agilent Inc, CA) was used for normalization and data transformation. Statistical Analysis of Microarray (SAM) and Prediction Analysis of Microarray (PAM) programs were used to analyze Agilent microarray data. T test and Jonckheere-Terpstra trend test were used to determine the specific genes for sub cell types by the ordinal rank of healthy donor (HD), spontaneous tolerance (SP), and induced tolerance (IN). Statistical analyses were done by SAS 9.3 software (Cary, N.C.).

II. Results

We identified 99 genes using the SAM (see Tusher, et al. supra) and PAM statistical analysis tool (Predictive Analysis of Microarray data, Tibshirani et al., Proc. Nat'l Acad. Sci. USA (2002) 99:6567-72) (FDR<2%) with highest predictive value in identifying a tolerogenic state in the blood samples. PAM is a statistical analysis program that identifies a minimum gene set characteristic of user defined sample groups (the learning set) and then scores both known and unknown samples based on similarity to identified expression profile differences.

The 99 genes identified are listed in Table 1 below. Also noted in Table I is whether the identified gene is associated with the TGF-β signaling pathway (p<0.0001 by hypergeometric) and/or with cell cycle regulation/signaling (p=0.0001 by hypergeometric); genes in both of these pathways whose expression correlates with graft tolerance were identified in a previous study using the Stanford Lymphochip (LC) micro-array (see Brouard et al., PNAS 2007, vol. 104, pp. 15448-15453).

Figure 1B:
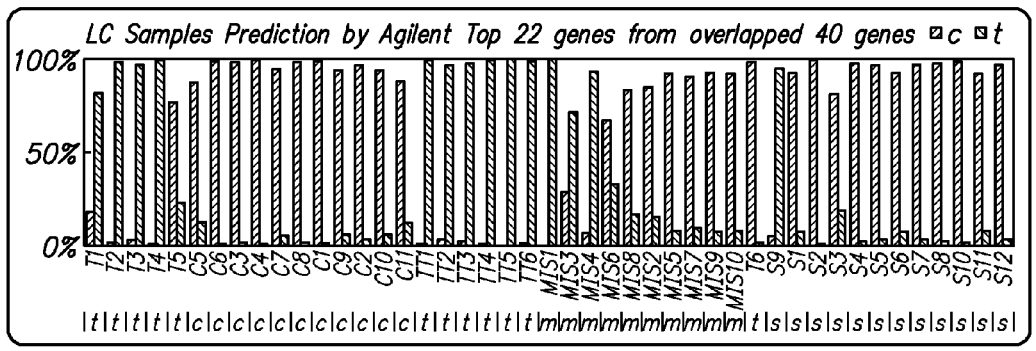
FIG. 1B shows prediction using 22 gene set of the present invention to re-classify the same LC samples. All re-analyzed samples in FIG. 1B were predicted as the same as in FIG. 1A except for MIS6 and MIS8, which have the trend of the TOL prediction.

Forty genes in Table 1 were identified in Brouard et al. using the LC platform, 2 of which were used as part of the 49 gene 'footprint' described therein (P=0.0085 by hypergeometric). FIG. 1A shows the classification of a set of samples using the LC 49 footprint prediction of the Brouard et al. study. From the overlapping 40 genes (i.e., between the 99 genes in Table 1 (using Agilent arrays) and those identified in the LC platform studies of Brouard et al. (using Stanford Lymphochip arrays)), the top 22 genes using PAM & SAM analyses (FDR<2%) were employed to re-classify the same LC samples shown in FIG. 1A. As shown in FIG. 1B, the 22 gene set gives similar predictions as the 49 gene set in FIG. 1A. Indeed, all samples were predicted as the same as 49 footprints, except for MIS6 and MIS8, which have the trend of the TOL prediction.

Figure 2:
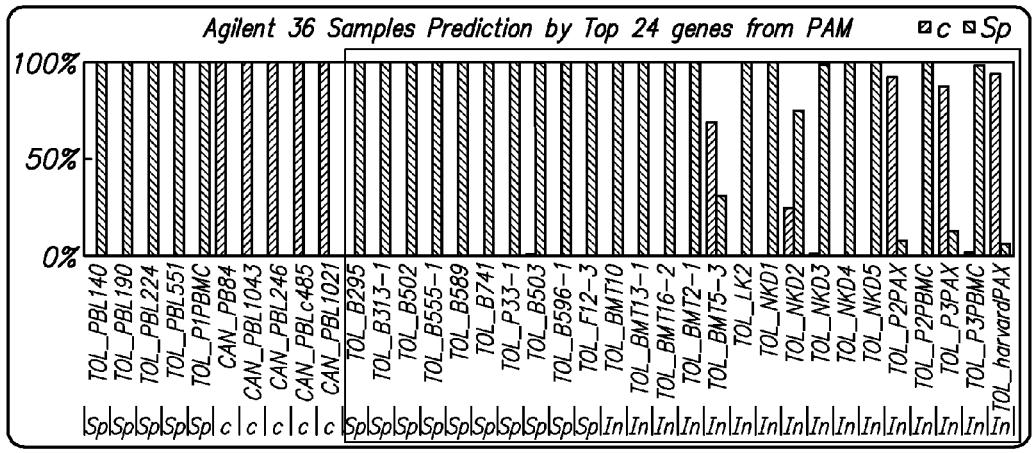
FIG. 2 provides sample predictions using the top 24 genes selected from the 99 genes in Table 1.
Figure 3:
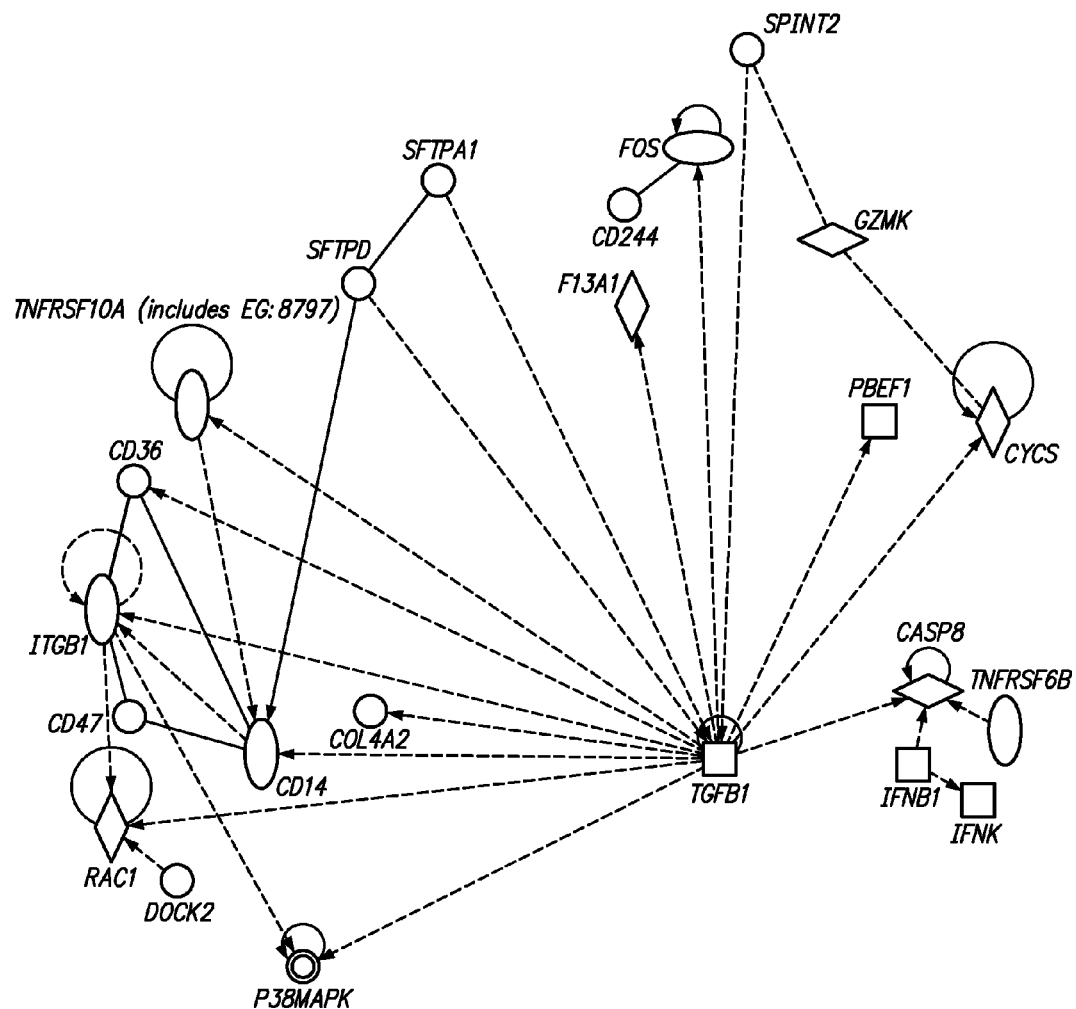
FIG. 3 shows the TGF-β signaling network for the top 24 genes from the 99 gene set in Table 1 identified in the analysis using the Agilent array platform.
Figure 4A:
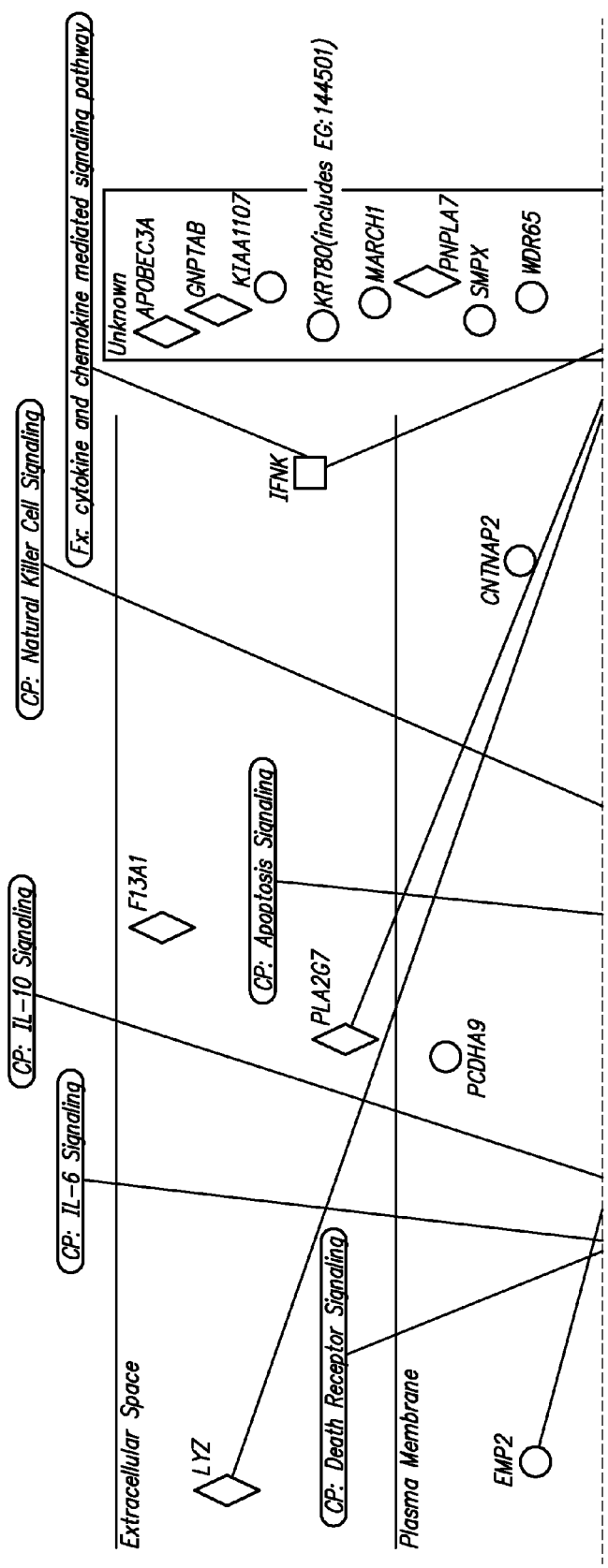
FIGS. 4A-4B show B, T, and NK cell signaling regulation for the top 24 genes from the 99 gene set in Table 1 identified in the analysis using the Agilent array platform.
Figure 4B:
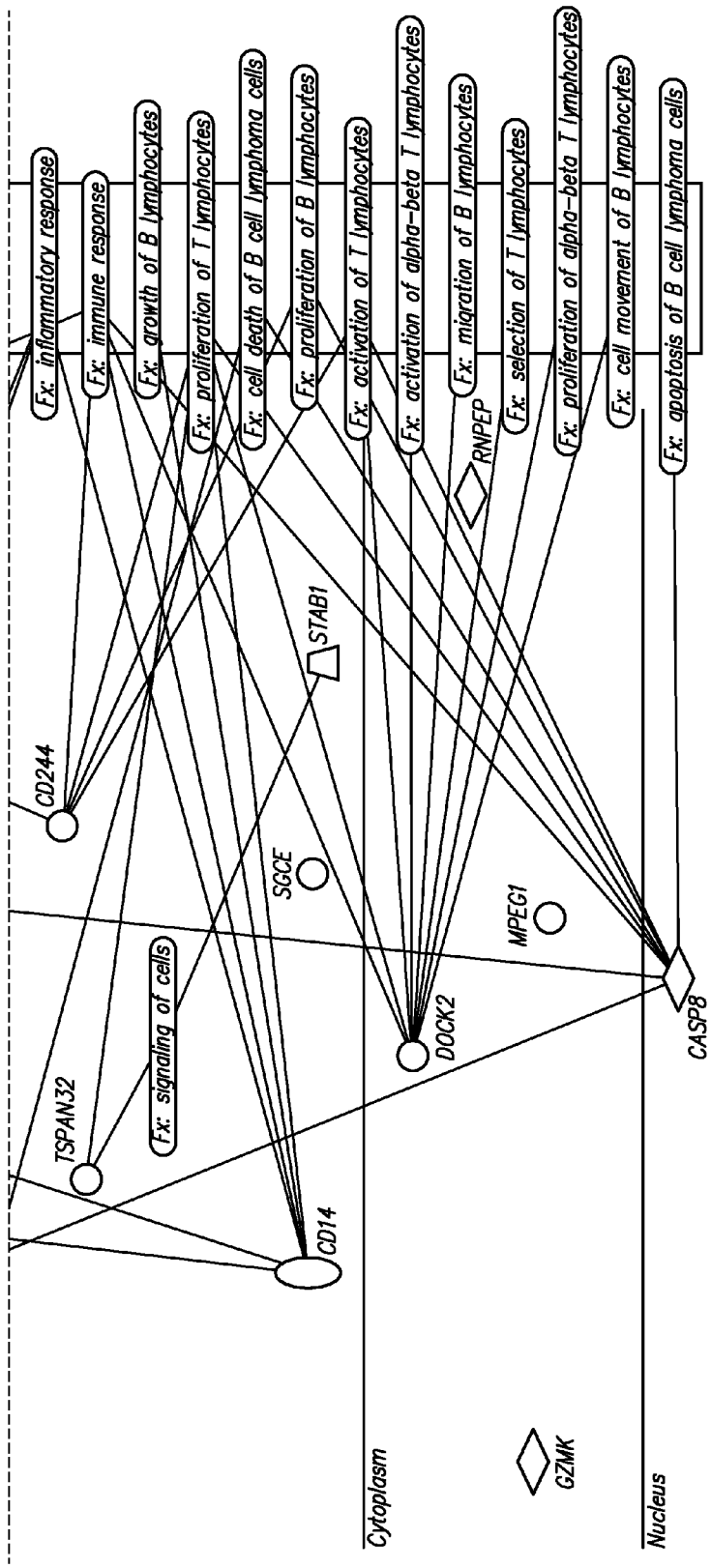

FIG. 2 provides sample predictions using the top 24 genes selected from the 99 genes in Table 1. In FIG. 2, the left panel shows the training set and the right panel shows the test set. All spontaneous samples are 100% predicted correctly using this 24 gene set. The LK2 induced patient (TOL_LK2) was predicted as SP-TOL, which has been confirmed by clinical observation. The patient has been off drug for 2 years.

TABLE 1

A list of the 99 genes identified that are differentially expressed in TOL vs. CAN. Genes involved in TGF-β and cell cycle signaling are indicated.

| Symbol | Entrez GeneID | fold | FDR (%) | TGF-b | Cell cycle | 24 genes |
|---|---|---|---|---|---|---|
| MARCH1 | 55016 | 3.0022797 | 0 | | | |
| ANGPTL1 | 9068 | −2.007214 | 0 | | | |
| ANKRD15 | 23189 | −2.0878 | 0 | | | |
| ANTXR1 | 84168 | −2.19655 | 1.1507317 | | | |
| APOBEC3A | 200315 | 7.3809241 | 0.5802009 | | | Y |
| APOC3 | 345 | −3.212175 | 1.1507317 | | | |
| ARL4C | 10123 | 2.4144416 | 0.5802009 | | | |
| ARRDC2 | 27106 | 2.2580325 | 0.5802009 | | | |
| BARD1 | 580 | −2.139497 | 0 | | | |
| BMPR1A | 657 | −2.797208 | 1.1507317 | Y | | |
| CAGE1 | 285782 | −2.69422 | 1.1507317 | | | |
| CASP8 | 841 | 3.1857514 | 0 | Y | | Y |
| CCNY | 219771 | 2.1650647 | 0.5802009 | | | |
| CD14 | 929 | 2.9491052 | 0 | Y | | Y |
| CD163 | 9332 | 3.9154456 | 0.9863415 | Y | | |
| CD244 | 51744 | 2.2280641 | 0 | | | Y |
| CD36 | 948 | 2.8681281 | 0.5802009 | Y | | |
| CDK5RAP3 | 80279 | 2.0183769 | 0 | | | |
| CNTNAP2 | 26047 | −5.192761 | 1.1507317 | | | Y |
| CXX1 | 8933 | −2.620834 | 1.1507317 | | | |
| CYP26A1 | 1592 | −2.769904 | 1.1507317 | | | |
| CYP4B1 | 1580 | −3.547685 | 1.1507317 | | | |
| DOCK2 | 1794 | 2.3320694 | 0 | | | Y |
| DYNC2LI1 | 51626 | −2.096258 | 0 | | | |
| EMP2 | 2013 | −2.701 | 1.1507317 | | | Y |
| EMR2 | 30817 | 3.166663 | 0.9863415 | | | |
| ENAH | 55740 | −2.891351 | 1.1507317 | | | |
| ETS2 | 2114 | 2.692491 | 0.5802009 | | | |
| F13A1 | 2162 | 3.1994918 | 0 | Y | | Y |
| FAM13A1OS | 285512 | 2.6713794 | 0.5802009 | | | |
| FLJ90086 | 389389 | −2.103278 | 1.1507317 | | | |
| FOSL2 | 2355 | 2.809 | 0.5802009 | Y | | |
| FOXC1 | 2296 | −6.621625 | 1.1507317 | Y | | |
| FTMT | 94033 | 2.0330983 | 0 | | | |
| GGTA1 | 2681 | 4.3356754 | 0.7671545 | | | |
| GNPTAB | 79158 | 2.3641187 | 0 | | | Y |
| GOLPH2 | 51280 | −2.853767 | 1.1507317 | | | |
| GPR125 | 166647 | −2.675509 | 1.1507317 | | | |
| GZMB | 3002 | 2.7880761 | 0.5802009 | | | |
| GZMK | 3003 | 3.179326 | 0 | | | Y |
| HLA-DQA2 | 3118 | 3.5716123 | 0.9863415 | | | |
| HSD17B6 | 8630 | −2.21751 | 1.1507317 | | | |
| IFNK | 56832 | −2.913018 | 0 | | | Y |
| IGHM | 3507 | 2.2203545 | 0.7671545 | | Y | |
| IPO13 | 9670 | −2.01756 | 0 | | | |
| ITIH4 | 3700 | 1.9524537 | 0 | | | |
| KRT17 | 3872 | −2.917036 | 1.1507317 | Y | | |
| KRT80 | 144501 | −2.621779 | 0 | | | Y |
| LAIR2 | 3904 | 2.7438641 | 0.5802009 | | | |
| LDHAL6A | 160287 | −2.371389 | 1.1507317 | | | |
| LGR6 | 59352 | 3.2632785 | 0.9863415 | | | |

TABLE 1-continued

A list of the 99 genes identified that are differentially expressed in TOL vs. CAN. Genes involved in TGF-β and cell cycle signaling are indicated.

| Symbol | Entrez GeneID | fold | FDR (%) | TGF-b | Cell cycle | 24 genes |
|---|---|---|---|---|---|---|
| LOC124245 | 124245 | 2.1722114 | 0.5802009 | | | |
| LOC150371 | 150371 | −3.532812 | 1.1507317 | | | |
| LOC283278 | 283278 | −2.818204 | 0 | | | |
| LOC400451 | 400451 | −2.543694 | 1.1507317 | | | |
| LOC440156 | 642477 | −2.310971 | 0 | | | |
| LOC541472 | 541472 | −3.541878 | 0 | | | Y |
| LOC55908 | 55908 | −1.76498 | 0 | | | |
| LOXL2 | 4017 | −4.541061 | 1.1507317 | Y | | |
| LRPAP1 | 4043 | 2.2859522 | 0 | | | |
| LYZ | 4069 | 2.8267647 | 0 | | | Y |
| MARCO | 8685 | 2.8601166 | 1.1365251 | | | |
| MLPH | 79083 | −2.58653 | 1.1507317 | | | |
| MPEG1 | 219972 | 3.2504029 | 0 | | | Y |
| MPZL1 | 9019 | −2.331467 | 1.1507317 | | | |
| MYO3A | 53904 | −2.950033 | 1.1507317 | | | |
| NCR1 | 9437 | 3.8883374 | 1.2148487 | | | |
| NEDD4L | 23327 | −2.623521 | 1.2148487 | | | |
| NLRP3 | 114548 | 3.7234615 | 0.5802009 | | | |
| PAICS | 10606 | −4.250718 | 1.2148487 | | | |
| PBLD | 64081 | −2.232983 | 0 | | | |
| PCDHA9 | 9752 | −2.634803 | 0 | | | Y |
| PHF1 | 5252 | 1.6854487 | 0 | | | |
| PLA2G7 | 7941 | 4.9729708 | 0 | | | Y |
| PLTP | 5360 | −2.266916 | 1.1507317 | | | |
| PNPLA7 | 375775 | −3.730196 | 1.1507317 | | | Y |
| PPBP | 5473 | 2.4655572 | 0.7671545 | | | |
| PRKCDBP | 112464 | −4.079189 | 1.1507317 | | | |
| REL | 5966 | 2.0806223 | 0 | | Y | |
| RNPEP | 6051 | 2.3243464 | 0 | | | Y |
| SCHIP1 | 29970 | −2.832874 | 1.1507317 | | | |
| SGCE | 8910 | −3.914326 | 0 | | | Y |
| SLC13A1 | 6561 | −3.412758 | 1.1507317 | | | |
| SMO | 6608 | −2.186908 | 0 | | | |
| SMPX | 23676 | −2.630361 | 0 | | | Y |
| SPATS1 | 221409 | −3.279478 | 1.1507317 | | | |
| STAB1 | 23166 | 2.9611082 | 0 | | | Y |
| STEAP1 | 26872 | −3.380256 | 1.1507317 | | | |
| TJP1 | 7082 | −3.399506 | 1.2148487 | Y | | |
| TNFSF13 | 8741 | 2.6887683 | 0.8908891 | | | |
| TPD52L3 | 89882 | −3.766346 | 1.6627545 | | | |
| TPX2 | 22974 | −1.955087 | 0 | | | |
| TSPAN32 | 10077 | 2.1335027 | 0 | | | Y |
| TUBA3C | 7278 | 2.4974196 | 0.5802009 | | | |
| WDR65 | 149465 | −3.843356 | 0 | | | Y |
| XKRX | 402415 | −2.744066 | 1.1507317 | | | |
| XRCC2 | 7516 | −2.979154 | 1.1507317 | Y | | |
| ZC3H11B | 643136 | 2.4800248 | 0.8908891 | | | |
| ZFP91 | 80829 | 2.2669509 | 0 | | | |

Figure 5:
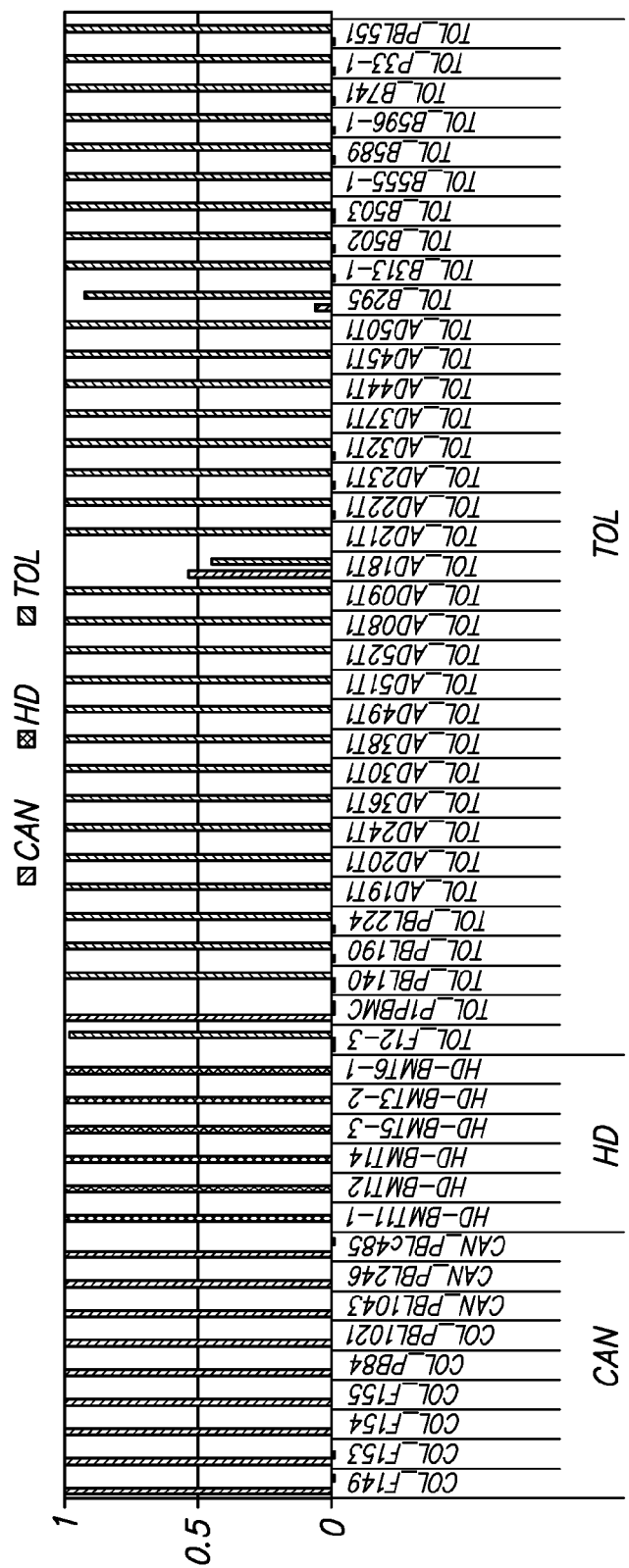
FIG. 5 shows 3-class prediction of HD vs. TOL vs. CAN samples based on the 28 gene set of Table 2.

In further analyses, we identified 28 genes using PAM and SAM analysis tools (FDR<5%) whose expression levels are the best predictors of 3 distinct subject classes, differentiating HD vs. SP vs. CAN (see Table 2, below). FIG. 5 shows 3-class prediction of HD vs. TOL vs. CAN samples based on this 28 gene set.

TABLE 2

List of 28 genes whose expression levels predict 3 distinct subject classes (HD vs. TOL vs. CAN).

| Symbol | Entrez Gene ID | HD vs. TOL vs. CAN |
|---|---|---|
| TP73 | 7161 | Y |
| CIRBP | 1153 | Y |
| VNN1 | 8876 | Y |
| ATXN1 | 6310 | Y |
| BMP2K | 55589 | Y |
| KIAA1324 | 57535 | Y |
| PLXNC1 | 10154 | Y |
| CCL3 | 6348 | Y |
| WNK1 | 65125 | Y |
| CCL3L3 | 414062 | Y |
| IL6 | 3569 | Y |
| MYL2 | 4633 | Y |
| KIF15 | 56992 | Y |
| IPO13 | 9670 | Y |
| TMEM117 | 84216 | Y |
| KIAA1609 | 57707 | Y |
| RUNX2 | 860 | Y |
| CBFA2T2 | 9139 | Y |
| TUBB4 | 10382 | Y |
| PDPN | 10630 | Y |
| PRPF40B | 25766 | Y |
| NRTN | 4902 | Y |

TABLE 2-continued

List of 28 genes whose expression levels predict
3 distinct subject classes (HD vs. TOL vs. CAN).

| Symbol | Entrez Gene ID | HD vs. TOL vs. CAN |
|---|---|---|
| KRT17 | 3872 | Y |
| TSPAN7 | 7102 | Y |
| CLGN | 1047 | Y |
| CCL2 | 6347 | Y |
| CENPN | 55839 | Y |
| DOPEY2 | 9980 | Y |

We then performed a sub analysis of the data for genes that are:

1) expressed in distinct T cell subsets, and 2) whose expression level is significantly different between HD vs. TOL (SP+IN) phenotypes or has significantly expression rank order by JT test among HD vs. SP vs. IN. T cell subsets were defined based on their expression of CD3, CD4, CD8, and CD45 markers (see Table 3). Table 3 lists 147 genes from JT test and SAM (FDR<5%) that are significantly differentially regulated for either HD vs. TOL (SP+IN) or HD vs. SP vs. IN and also shows their specific T cell subset expression patterns.

TABLE 3

A gene list (147 genes) of either significantly differentially expressed between HD vs. TOL (SP + IN) or has significantly expression rank order by JT test among HD vs. Spontaneous tolerance (SP) vs. Induced tolerance (IN) with specific 5 different cell types.

| Sybmol | Entrez Gene ID | Z_JT | P value JT | FDR HD-TOL (%) | HD vs TOL | trends of HD vs SP vs IN | CD3+ | CD4+/ CD8+ | CD45+/ CD45− |
|---|---|---|---|---|---|---|---|---|---|
| CNIH | 10175 | −1.14459 | 0.25238 | 3.045626145 | Y | | CD3+ | CD4+ | |
| CD8B | 926 | 2.55331 | 0.01067 | 1.640686369 | Y | Y | CD3+ | CD8+ | |
| HNRPLL | 92906 | −1.60242 | 0.10906 | 0.215406287 | Y | | CD3+ | | Naïve |
| PVRL3 | 25945 | −3.1168 | 0.00183 | 0.121036585 | Y | Y | CD3+ | | Naïve |
| ANK3 | 288 | −2.342 | 0.01918 | 50 | | Y | CD3+ | | |
| C6orf15 | 84830 | −3.01114 | 0.0026 | 0.882047023 | | Y | CD3+ | | |
| DUSP16 | 80824 | −2.13069 | 0.03311 | 50 | | Y | CD3+ | | |
| IER5L | 389792 | 2.02504 | 0.04286 | 50 | | Y | CD3+ | | |
| INPP4B | 8821 | −2.02504 | 0.04286 | 50 | | Y | CD3+ | | |
| KIAA391 | 9692 | 2.44765 | 0.01438 | 50 | | Y | CD3+ | | |
| NPDC1 | 56654 | 2.55331 | 0.01067 | 50 | | Y | CD3+ | | |
| PRKCA | 5578 | −2.87027 | 0.0041 | 1.640686369 | | Y | CD3+ | | |
| TRPC1 | 7220 | −1.98982 | 0.04661 | 50 | | Y | CD3+ | | |
| ANK3 | 288 | −2.44765 | 0.01438 | 4.215733066 | Y | Y | CD3+ | | |
| C13orf15 | 28984 | −0.33457 | 0.73795 | 3.53567017 | Y | | CD3+ | | |
| C17orf48 | 56985 | −0.93328 | 0.35068 | 1.640686369 | Y | | CD3+ | | |
| C18orf17 | 125488 | −0.86284 | 0.38822 | 2.310988327 | Y | | CD3+ | | |
| C1orf54 | 79630 | −1.84895 | 0.06447 | 0.083225156 | Y | | CD3+ | | |
| CCDC14 | 112942 | −2.44765 | 0.01438 | 0.121036585 | Y | Y | CD3+ | | |
| CCDC19B | 55013 | −0.72197 | 0.47031 | 4.215733066 | Y | | CD3+ | | |
| CD28 | 940 | −1.81373 | 0.06972 | 1.104381518 | Y | | CD3+ | | |
| CD48 | 962 | −0.93328 | 0.35068 | 3.045626145 | Y | | CD3+ | | |
| CD6 | 923 | −1.10937 | 0.26727 | 3.53567017 | Y | | CD3+ | | |
| CDR2 | 1039 | −1.10937 | 0.26727 | 2.674788698 | Y | | CD3+ | | |
| CITED4 | 163732 | −0.65153 | 0.5147 | 1.931533662 | Y | | CD3+ | | |
| DCTN6 | 10671 | −0.9685 | 0.3328 | 0.277544618 | Y | | CD3+ | | |
| DCTN6 | 10671 | −1.25024 | 0.21121 | 0.124017782 | Y | | CD3+ | | |
| DNAJB1 | 3337 | −0.61632 | 0.53769 | 1.104381518 | Y | | CD3+ | | |
| DYNLT3 | 6990 | −1.32068 | 0.18661 | 0.193782756 | Y | | CD3+ | | |
| EFCAB4A | 283229 | −1.67286 | 0.09436 | 0.193782756 | Y | | CD3+ | | |
| FAM84B | 157638 | −2.342 | 0.01918 | 0.407822995 | Y | Y | CD3+ | | |
| FXYD5 | 53827 | −0.36979 | 0.71154 | 2.674788698 | Y | | CD3+ | | |
| GAS5 | 60674 | −1.5672 | 0.11707 | 0.121036585 | Y | | CD3+ | | |
| GPRASP1 | 9737 | −2.37722 | 0.01744 | 0.882047023 | Y | Y | CD3+ | | |
| HECA | 51696 | −1.03893 | 0.29884 | 0.407822995 | Y | | CD3+ | | |
| HLF | 3131 | −2.58853 | 0.00964 | 0.121036585 | Y | Y | CD3+ | | |
| IL23A | 51561 | −2.06026 | 0.03937 | 0.407822995 | Y | Y | CD3+ | | |
| KIAA48 | 9729 | −2.41244 | 0.01585 | 0.596694647 | Y | Y | CD3+ | | |
| NELL2 | 4753 | −2.23635 | 0.02533 | 4.215733066 | Y | Y | CD3+ | | |
| NGFRAP1L1 | 340542 | −1.98982 | 0.04661 | 1.104381518 | Y | Y | CD3+ | | |
| OCIAD2 | 132299 | −1.9546 | 0.05063 | 0.707577565 | Y | | CD3+ | | |
| PBX4 | 80714 | −0.26414 | 0.79168 | 3.045626145 | Y | | CD3+ | | |
| PVRL3 | 25945 | −1.60242 | 0.10906 | 0.407822995 | Y | | CD3+ | | |
| RGS1 | 6001 | −1.81373 | 0.06972 | 0.596694647 | Y | | CD3+ | | |
| SFXN1 | 94081 | −0.05283 | 0.95787 | 2.310988327 | Y | | CD3+ | | |
| SGTB | 54557 | −1.74329 | 0.08128 | 1.342763357 | Y | | CD3+ | | |
| SH3YL1 | 26751 | −1.70807 | 0.08762 | 3.53567017 | Y | | CD3+ | | |
| SLC26A11 | 284129 | −0.9685 | 0.3328 | 0.882047023 | Y | | CD3+ | | |
| SPOCK2 | 9806 | −0.82762 | 0.40788 | 2.310988327 | Y | | CD3+ | | |
| TMEM3B | 161291 | −1.84895 | 0.06447 | 0.596694647 | Y | | CD3+ | | |
| TMEM66 | 51669 | −1.5672 | 0.11707 | 0.707577565 | Y | | CD3+ | | |
| TNFAIP8 | 25816 | −1.32068 | 0.18661 | 2.310988327 | Y | | CD3+ | | |
| TULP3 | 7289 | −0.72197 | 0.47031 | 0.707577565 | Y | | CD3+ | | |
| ZC3H6 | 376940 | −2.20113 | 0.02773 | 0.407822995 | Y | Y | CD3+ | | |
| ZNF563 | 147837 | −2.09547 | 0.03613 | 1.342763357 | Y | Y | CD3+ | | |

TABLE 3-continued

A gene list (147 genes) of either significantly differentially expressed between HD vs.
TOL (SP + IN) or has significantly expression rank order by JT test among HD vs. Spontaneous
tolerance (SP) vs. Induced tolerance (IN) with specific 5 different cell types.

| Symbol | Entrez Gene ID | Z_JT | P value JT | FDR HD-TOL (%) | HD vs TOL | trends of HD vs SP vs IN | CD3+ | CD4+/ CD8+ | CD45+/ CD45− |
|---|---|---|---|---|---|---|---|---|---|
| TRIB1 | 10221 | −1.03893 | 0.29884 | 1.342763357 | Y | | | CD4+ | Naïve |
| ZMIZ1 | 57178 | −1.63764 | 0.1015 | 0.407822995 | Y | | | CD4+ | Naïve |
| ARHGEF1L | 55160 | 2.55331 | 0.01067 | 50 | | Y | | CD4+ | |
| STAB1 | 23166 | 2.342 | 0.01918 | 50 | | Y | | CD4+ | |
| TRIM7 | 81786 | 2.02504 | 0.04286 | 50 | | Y | | CD4+ | |
| B3GNT5 | 84002 | −1.35589 | 0.17513 | 0.707577565 | Y | | | CD4+ | |
| CD3LF | 146722 | 0.36979 | 0.71154 | 4.79008092 | Y | | | CD4+ | |
| CENTG3 | 116988 | −1.35589 | 0.17513 | 1.931533662 | Y | | | CD4+ | |
| CLEC7A | 64581 | −0.82762 | 0.40788 | 2.310988327 | Y | | | CD4+ | |
| CSF1R | 1436 | 0.61632 | 0.53769 | 4.215733066 | Y | | | CD4+ | |
| CTSS | 1520 | 2.83505 | 0.00458 | 0.124017782 | Y | Y | | CD4+ | |
| EAF2 | 55840 | −0.51066 | 0.60959 | 4.215733066 | Y | | | CD4+ | |
| ETS2 | 2114 | −1.21502 | 0.22436 | 0.882047023 | Y | | | CD4+ | |
| GNB4 | 59345 | −0.89806 | 0.36915 | 1.104381518 | Y | | | CD4+ | |
| IFNAR2 | 3455 | 2.37722 | 0.01744 | 0.596694647 | Y | Y | | CD4+ | |
| IRAK3 | 11213 | −0.65153 | 0.5147 | 1.104381518 | Y | | | CD4+ | |
| KIF13A | 63971 | −0.15848 | 0.87408 | 3.53567017 | Y | | | CD4+ | |
| MAFB | 9935 | −1.1798 | 0.23808 | 0.707577565 | Y | | | CD4+ | |
| SMPDL3A | 10924 | −1.10937 | 0.26727 | 0.882047023 | Y | | | CD4+ | |
| TBC1D8 | 11138 | −0.75719 | 0.44894 | 2.674788698 | Y | | | CD4+ | |
| TRIB1 | 10221 | −1.25024 | 0.21121 | 0.215406287 | Y | | | CD4+ | |
| DKK3 | 27122 | 2.06026 | 0.03937 | 50 | | Y | | CD8+ | |
| ARHGAP8 | 23779 | −1.60242 | 0.10906 | 1.640686369 | Y | | | CD8+ | |
| AUTS2 | 26053 | −2.16591 | 0.03032 | 2.310988327 | Y | Y | | CD8+ | |
| C1orf21 | 81563 | −1.77851 | 0.07532 | 0.882047023 | Y | | | CD8+ | |
| CRTAM | 56253 | 2.02504 | 0.04286 | 1.931533662 | Y | Y | | CD8+ | |
| DKK3 | 27122 | −1.60242 | 0.10906 | 1.342763357 | Y | | | CD8+ | |
| EDG8 | 53637 | 2.37722 | 0.01744 | 1.931533662 | Y | Y | | CD8+ | |
| PPP1R16B | 26051 | −0.29935 | 0.76467 | 0.596694647 | Y | | | CD8+ | |
| RUNX3 | 864 | −0.68675 | 0.49224 | 1.342763357 | Y | | | CD8+ | |
| SYTL2 | 54843 | −1.67286 | 0.09436 | 3.53567017 | Y | | | CD8+ | |
| VCAM1 | 7412 | −1.74329 | 0.08128 | 0.596694647 | Y | | | CD8+ | |
| ZNF364 | 27246 | −2.02504 | 0.04286 | 0 | Y | Y | | CD8+ | |
| ANXA2 | 302 | 2.55331 | 0.01067 | 50 | | Y | | | Naïve |
| ANXA2P1 | 303 | 2.62374 | 0.0087 | 50 | | Y | | | Naïve |
| CD58 | 965 | −2.27156 | 0.02311 | 50 | | Y | | | Naïve |
| CD99 | 4267 | 2.79983 | 0.00511 | 50 | | Y | | | Naïve |
| CYB561 | 1534 | 2.44765 | 0.01438 | 50 | | Y | | | Naïve |
| CYB561 | 1534 | 2.79983 | 0.00511 | 50 | | Y | | | Naïve |
| FAM11C | 548322 | −2.58853 | 0.00964 | 0.882047023 | | Y | | | Naïve |
| FAM38A | 9780 | 2.02504 | 0.04286 | 50 | | Y | | | Naïve |
| PDIA6 | 10130 | 2.76462 | 0.0057 | 50 | | Y | | | Naïve |
| PLEKHA2 | 59339 | 2.09547 | 0.03613 | 50 | | Y | | | Naïve |
| TUBB2C | 10383 | 2.27156 | 0.02311 | 50 | | Y | | | Naïve |
| AHR | 196 | −0.54588 | 0.58515 | 2.674788698 | Y | | | | Naïve |
| ARHGDIA | 396 | −1.77851 | 0.07532 | 0.121036585 | Y | | | | Naïve |
| B4GALT1 | 2683 | −0.47544 | 0.63447 | 1.640686369 | Y | | | | Naïve |
| CHMP2B | 25978 | −1.88416 | 0.05954 | 0.882047023 | Y | | | | Naïve |
| CREM | 1390 | −0.79241 | 0.42812 | 0.215406287 | Y | | | | Naïve |
| CREM | 1390 | −1.53198 | 0.12553 | 0 | Y | | | | Naïve |
| DYNLT3 | 6990 | −1.91938 | 0.05494 | 0 | Y | | | | Naïve |
| ELL2 | 22936 | −2.09547 | 0.03613 | 0.121036585 | Y | Y | | | Naïve |
| EPAS1 | 2034 | −1.14459 | 0.25238 | 4.215733066 | Y | | | | Naïve |
| FTH1 | 2495 | −1.32068 | 0.18661 | 1.342763357 | Y | | | | Naïve |
| FTH1 | 2495 | −1.10937 | 0.26727 | 3.53567017 | Y | | | | Naïve |
| FTHL17 | 53940 | −1.5672 | 0.11707 | 0.124017782 | Y | | | | Naïve |
| GNA13 | 10672 | −0.93328 | 0.35068 | 0.277544618 | Y | | | | Naïve |
| GNG2 | 54331 | −1.77851 | 0.07532 | 0.882047023 | Y | | | | Naïve |
| HN1 | 51155 | 2.23635 | 0.02533 | 0.707577565 | Y | Y | | | Naïve |
| HNRPLL | 92906 | −0.89806 | 0.36915 | 0.277544618 | Y | | | | Naïve |
| IL2 | 3558 | −1.49677 | 0.13445 | 0.124017782 | Y | | | | Naïve |
| IL4I1 | 259307 | −1.03893 | 0.29884 | 0.882047023 | Y | | | | Naïve |
| IL8 | 3576 | −2.83505 | 0.00458 | 0 | Y | Y | | | Naïve |
| ITGB1 | 3688 | −0.36979 | 0.71154 | 1.640686369 | Y | | | | Naïve |
| KLF8 | 11279 | 2.30678 | 0.02107 | 1.342763357 | Y | Y | | | Naïve |
| LATS2 | 26524 | −1.1798 | 0.23808 | 2.310988327 | Y | | | | Naïve |
| LRP12 | 29967 | −2.37722 | 0.01744 | 0 | Y | Y | | | Naïve |
| MAF | 4094 | −1.28546 | 0.19863 | 4.79008092 | Y | | | | Naïve |
| MAP3K8 | 1326 | −1.25024 | 0.21121 | 0.083225156 | Y | | | | Naïve |
| MYO1F | 4542 | 1.5672 | 0.11707 | 4.215733066 | Y | | | | Naïve |
| NAB1 | 4664 | −1.39111 | 0.16419 | 0.121036585 | Y | | | | Naïve |
| NRAS | 4893 | −0.36979 | 0.71154 | 2.310988327 | Y | | | | Naïve |

TABLE 3-continued

A gene list (147 genes) of either significantly differentially expressed between HD vs. TOL (SP + IN) or has significantly expression rank order by JT test among HD vs. Spontaneous tolerance (SP) vs. Induced tolerance (IN) with specific 5 different cell types.

| Symbol | Entrez Gene ID | Z_JT | P value JT | FDR HD-TOL (%) | HD vs TOL | trends of HD vs SP vs IN | CD3+ | CD4+/CD8+ | CD45+/CD45− |
|---|---|---|---|---|---|---|---|---|---|
| OGFRL1 | 79627 | −1.5672 | 0.11707 | 1.640686369 | Y | | | | Naïve |
| PANX1 | 24145 | −0.9685 | 0.3328 | 0.882047023 | Y | | | | Naïve |
| PBEF1 | 10135 | −2.20113 | 0.02773 | 0.407822995 | Y | Y | | | Naïve |
| PIK3R1 | 5295 | −0.75719 | 0.44894 | 1.640686369 | Y | | | | Naïve |
| PLEKHA5 | 54477 | −1.9546 | 0.05063 | 0.707577565 | Y | | | | Naïve |
| PLXND1 | 23129 | −0.40501 | 0.68547 | 2.310988327 | Y | | | | Naïve |
| PRNP | 5621 | −1.63764 | 0.1015 | 0.193782756 | Y | | | | Naïve |
| SAT1 | 6303 | −1.53198 | 0.12553 | 0.121036585 | Y | | | | Naïve |
| SLC39A8 | 64116 | −2.27156 | 0.02311 | 0.193782756 | Y | Y | | | Naïve |
| SPTLC1 | 10558 | −2.23635 | 0.02533 | 0.124017782 | Y | Y | | | Naïve |
| SRGN | 5552 | −2.16591 | 0.03032 | 0.707577565 | Y | Y | | | Naïve |
| STAM | 8027 | −0.89806 | 0.36915 | 0.596694647 | Y | | | | Naïve |
| SUB1 | 10923 | −1.49677 | 0.13445 | 0.121036585 | Y | | | | Naïve |
| SUB1 | 10923 | −1.25024 | 0.21121 | 0.124017782 | Y | | | | Naïve |
| TGFB1 | 7040 | −1.35589 | 0.17513 | 0.121036585 | Y | | | | Naïve |
| TIMP1 | 7076 | −0.29935 | 0.76467 | 3.045626145 | Y | | | | Naïve |
| TMED5 | 50999 | −0.86284 | 0.38822 | 0.596694647 | Y | | | | Naïve |
| TPM4 | 7171 | −0.5811 | 0.56117 | 2.674788698 | Y | | | | Naïve |
| YWHAZ | 7534 | −1.39111 | 0.16419 | 4.79008092 | Y | | | | Naïve |
| ZNF365 | 22891 | −2.7294 | 0.00635 | 1.104381518 | Y | Y | | | Naïve |

Figure 6:
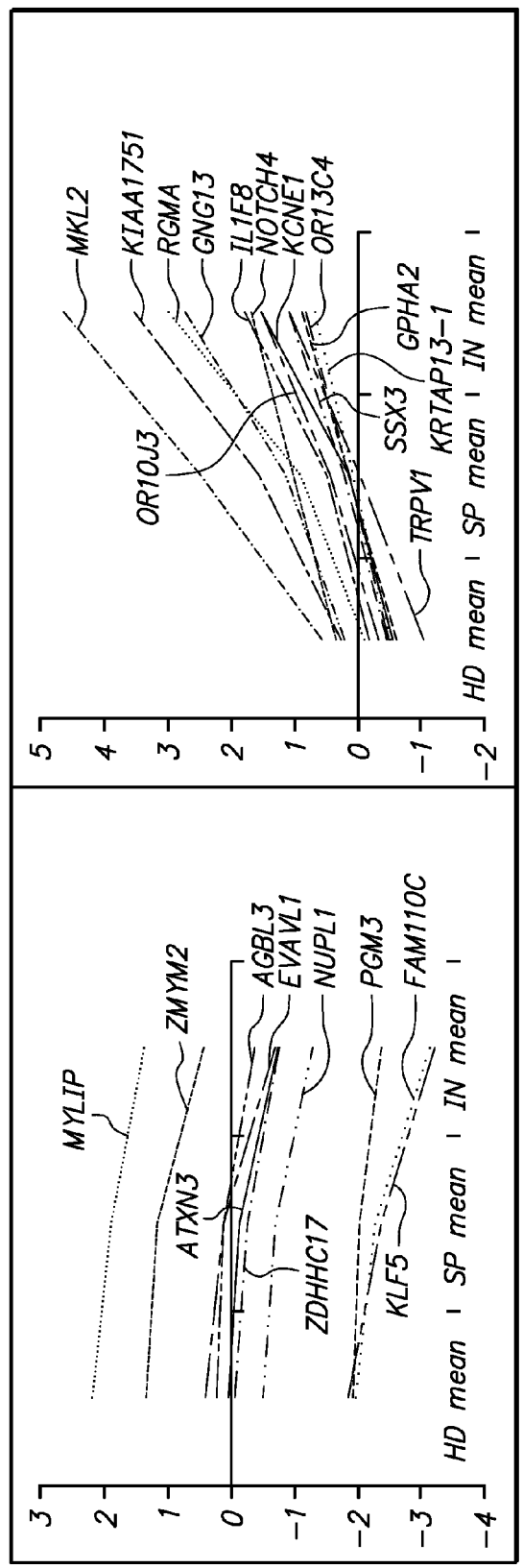
FIG. 6 shows the gene expression trends between HD vs. SP vs. IN of the genes in Table 4. Significantly down-regulated genes are shown in the left panel and up regulated genes are shown in the right panel.

We then performed another sub-analysis using PAM and SAM (FDR<2%) to identify genes whose expression shows significantly upward or downward trends in HD vs. SP vs. IN (see Table 4, below). FIG. 6 shows the gene expression trends of these significantly down-regulated genes (left panel) and up regulated genes (right panel) between HD vs. SP vs. IN. As shown in Table 4, one gene (FAM110C) is known to be differentially expressed in Naive T cells.

TABLE 4

A gene list (24 genes) of significant differentially expressed either up or down among 3-class (HD vs. SP vs. IN)

| gene | Entrez Gene ID | Z_JT | P value JT | HD −> SP −> IN | CD3+ | CD4+/CD8+ | CD45+/CD45− |
|---|---|---|---|---|---|---|---|
| AGBL3 | 340351 | −3.50419 | 0.00046 | Y | | | |
| ELAVL1 | 1994 | −3.50419 | 0.00046 | Y | | | |
| NUPL1 | 9818 | −3.39854 | 0.00068 | Y | | | |
| KLF5 | 688 | −3.22245 | 0.00127 | Y | | | |
| MYLIP | 29116 | −3.22245 | 0.00127 | Y | | | |
| ATXN3 | 4287 | −3.15201 | 0.00162 | Y | | | |
| ZDHHC17 | 23390 | −2.97592 | 0.00292 | Y | | | |
| PGM3 | 5238 | −2.87027 | 0.0041 | Y | | | |
| ZMYM2 | 7750 | −2.76462 | 0.0057 | Y | | | |
| FAM110C | 642273 | −2.58853 | 0.00964 | Y | | | Naïve |
| OR10J3 | 441911 | 3.25767 | 0.00112 | Y | | | |
| SSX3 | 10214 | 3.25767 | 0.00112 | Y | | | |
| GNG13 | 51764 | 3.29289 | 0.00099 | Y | | | |
| KIAA1751 | 85452 | 3.3281 | 0.00087 | Y | | | |
| RGMA | 56963 | 3.36332 | 0.00077 | Y | | | |
| IL1F8 | 27177 | 3.43376 | 0.0006 | Y | | | |
| GPHA2 | 170589 | 3.53941 | 0.0004 | Y | | | |
| MKL2 | 57496 | 3.57463 | 0.00035 | Y | | | |
| TRPV1 | 7442 | 3.64507 | 0.00027 | Y | | | |
| KRTAP13-1 | 140258 | 3.75072 | 0.00018 | Y | | | |
| NOTCH4 | 4855 | 3.78594 | 0.00015 | Y | | | |
| OR13C4 | 138804 | 3.82116 | 0.00013 | Y | | | |
| KCNE1 | 3753 | 3.96203 | 0.00007 | Y | | | |

Identification of a large number of differentially expressed genes reported in this study of spontaneously tolerant adult renal transplant patients provides several biomarkers for spontaneously achieved immune tolerance. The gene expression study reported here shows that expression differences characteristic of spontaneously achieved tolerance can be detected in whole blood lysates obviating the need for more invasive methods of sampling.

It is evident that subject invention provides a convenient and effective way of determining whether a subject has a graft tolerant phenotype, without first removing the subject from immunosuppressive therapy. As such, the subject invention provides a number of distinct benefits, including the ability to easily identify subjects undergoing immunosuppressive therapy that have a graft tolerant phenotype, and therefore may be removed from immunosuppressive therapy, so that these individuals can avoid the adverse conditions, as well as costs, associated with such therapy. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of evaluating the expression levels of at least 5 genes selected from the group consisting of FAM110C, VNN1, ATXN1, BMP2K, CCL3L3, MYL2, KIF15, IPO13, TMEM117, PDPN, PRPF4OB, NRTN, TSPAN7, CENPN, DOPEY2, AGBL3, ELAVL1, NUPL1, KLF5, MYLIP, ATXN3, ZDHHC17, PGM3, ZMYM2, OR10J3, SSX3, GNG13, KIAA1751, RGMA, IL1F8, GPHA2, MKL2, TRPV1, KRTAP13-1, OR13C4, and KCNE1, comprising:
providing a sample from a subject who has received an allograft;
contacting said sample with a collection of gene specific primers designed to selectively amplify expression products of said at least 5 genes,
wherein the at least 5 genes includes FAM110C;
wherein the primers are labelled and the collection of gene specific primers comprises primers for selectively amplifying the at least 5 genes; and
assessing, using said collection of gene specific primers, the amount of said expression products in said sample.

2. The method according to claim 1, wherein said allograft is a renal allograft.

3. The method according to claim 1, wherein said sample is a blood sample.

4. The method according to claim 3, wherein said blood sample is a peripheral blood lymphocyte sample.

5. The method according to claim 1, wherein said expression products are nucleic acid transcripts.

6. The method according to claim 5, wherein said evaluating step comprises performing a RT-PCR assay.

7. The method according to claim 1, wherein the expression levels of FAM110C and at least 10 genes from the group are evaluated.

8. The method according to claim 1, wherein the expression levels of FAM110C and all of the genes from the group are evaluated.

9. The method according to claim 1, wherein said assessing is quantitative.

* * * * *